US00PP16620P3

(12) United States Plant Patent
Simmons et al.

(10) Patent No.: US PP16,620 P3
(45) Date of Patent: Jun. 6, 2006

(54) APPLE TREE NAMED 'PV 1027'

(50) Latin Name: *Malus sylvestris*
Varietal Denomination: PV 1027

(75) Inventors: Daniel Simmons, Rogers, OH (US); Paul Simmons, East Palastine, OH (US)

(73) Assignee: International Plant Management, Inc., Lawrence, MI (US)

( * ) Notice: Subject to any disclaimer, the term of this patent is extended or adjusted under 35 U.S.C. 154(b) by 0 days.

(21) Appl. No.: 10/822,202

(22) Filed: Apr. 12, 2004

(65) Prior Publication Data

US 2005/0229277 P1 Oct. 13, 2005

(51) Int. Cl.
*A01H 5/00* (2006.01)

(52) U.S. Cl. ..... Plt./161

(58) Field of Classification Search ..... Plt./173, Plt./161

See application file for complete search history.

(56) References Cited

U.S. PATENT DOCUMENTS

PP14,375 P2 * 12/2003 Warren ..... Plt./173
2004/0205868 P1 * 10/2004 Zima ..... Plt./173

* cited by examiner

*Primary Examiner*—Kent Bell
*Assistant Examiner*—W. C. Haas

(57) ABSTRACT

A new and distinct variety of apple tree, 'PV 1027,' originating as a mutation of the *Malus sylvestris* variety of 'Arends' (U.S. Plant Pat. No. 2,800). This new variety is unique from its parent because the fruit ripens 7 to 9 days before the parent and presents a larger, more reniform shape with a shinier finish.

3 Drawing Sheets

Botanical designation: *Malus sylvestris*.
Variety denomination: 'PV 1027'.

BACKGROUND OF THE INVENTION

A new and distinct variety of apple tree originating as a mutation of the *Malus sylvestris* variety of 'Arends' (U.S. Plant Pat. No. 2,800), hereinafter referred to as the 'PV 1027'. The new variety was found in a cultivated area where clones of 'Arends' (U.S. Plant Pat. No. 2,800) had been planted exclusively. The claimed plant is a budded scion of 'Arends' (U.S. Plant Pat. No. 2,800) that developed with different characteristics than 'Arends' (U.S. Plant Pat. No. 2,800). This new sport is unique from its parent because it ripens 7 to 9 days earlier and is significantly larger with a more reniform shape. The skin of the new variety is also considerably shinier than the parent.

BRIEF SUMMARY OF THE INVENTION

This new and distinctive strain of apple tree produces a fruit with solid red color covering 90% of the fruit surface, compared to 40% to 50% of the parent, 'Arends' (U.S. Plant Pat. No. 2,800). This new variety also ripens 7 to 9 days earlier than the parent and has a larger more reniform shape with a shinier finish. This new variety of apple tree was discovered in a cultivated area in 1997 in Rogers Ohio. In 1998, buds were taken from the original tree and propagated by chip budding into 50 trees. These trees were produced in Brentwood, Calif. This new cultivar has been reproduced by chip budding on 'Malling 9-337' and 'Malling 9 NIC 29' rootstocks and remains true to the description herein contained. The new variety has not been grown on its own root.

BRIEF DESCRIPTION OF THE DRAWINGS

The accompanying photographs show typical specimens of the new variety as depicted in color as nearly true as is reasonably possible in color illustrations of this character. These specimens were obtained in Rogers, Ohio.

The first drawing illustrates the fruits and foliage of the new variety at maturity.

Figure 1:
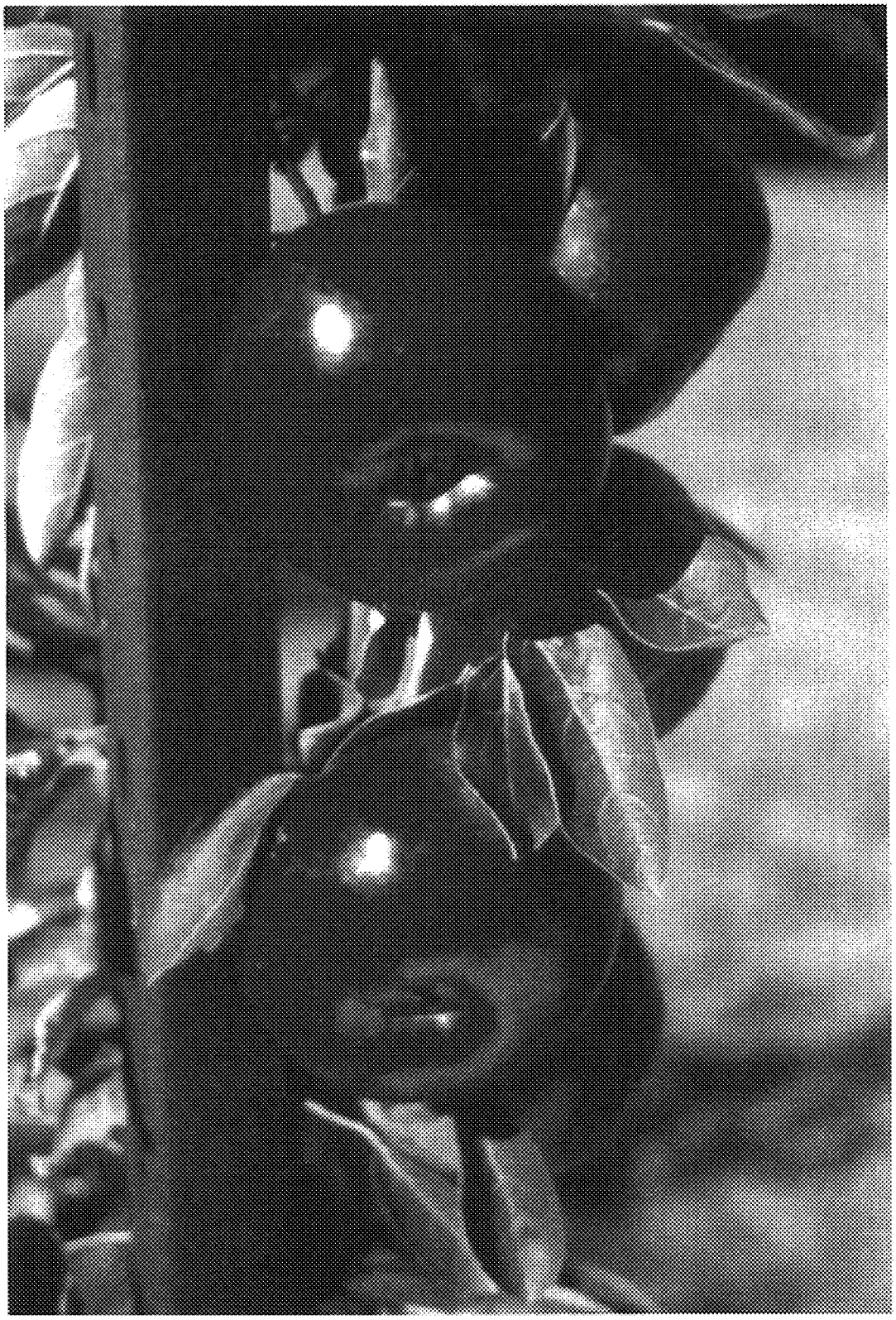
Figure 2:
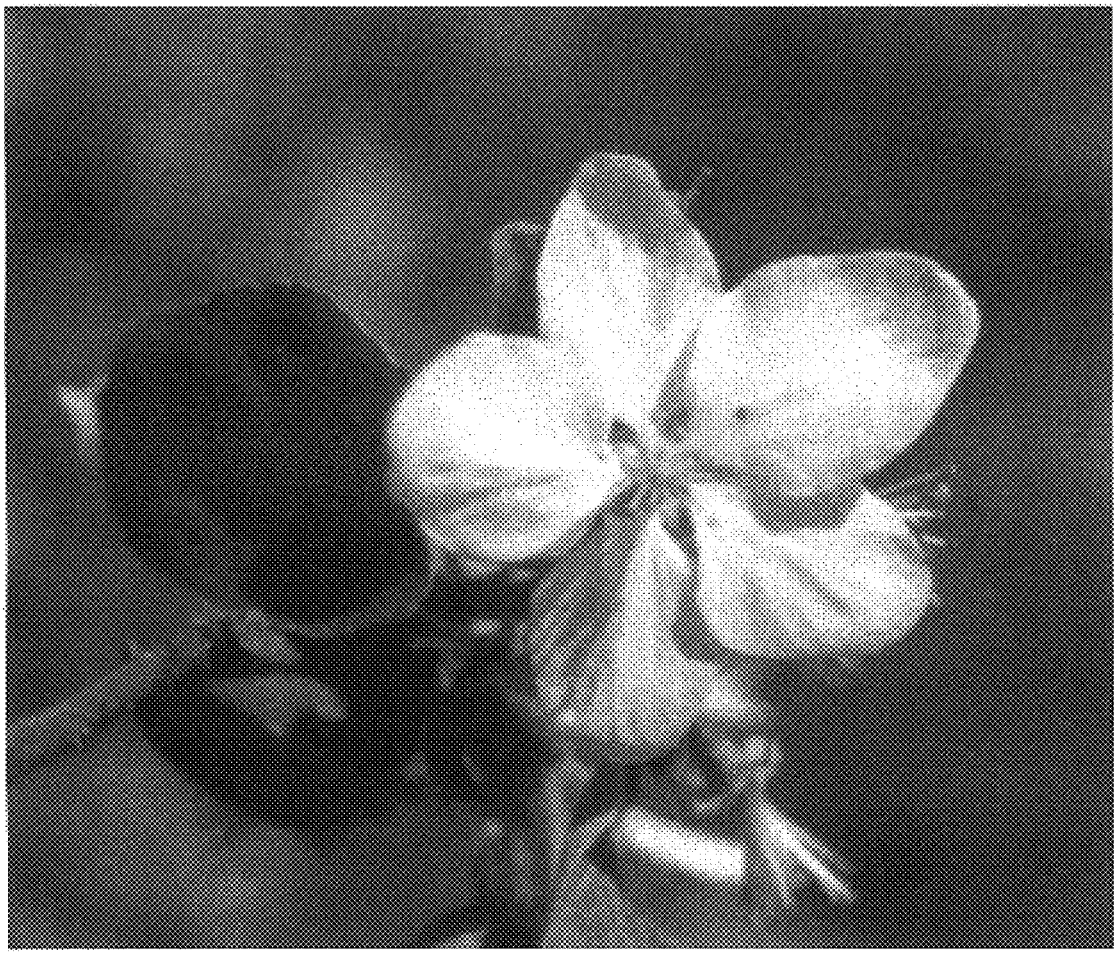
Figure 3:
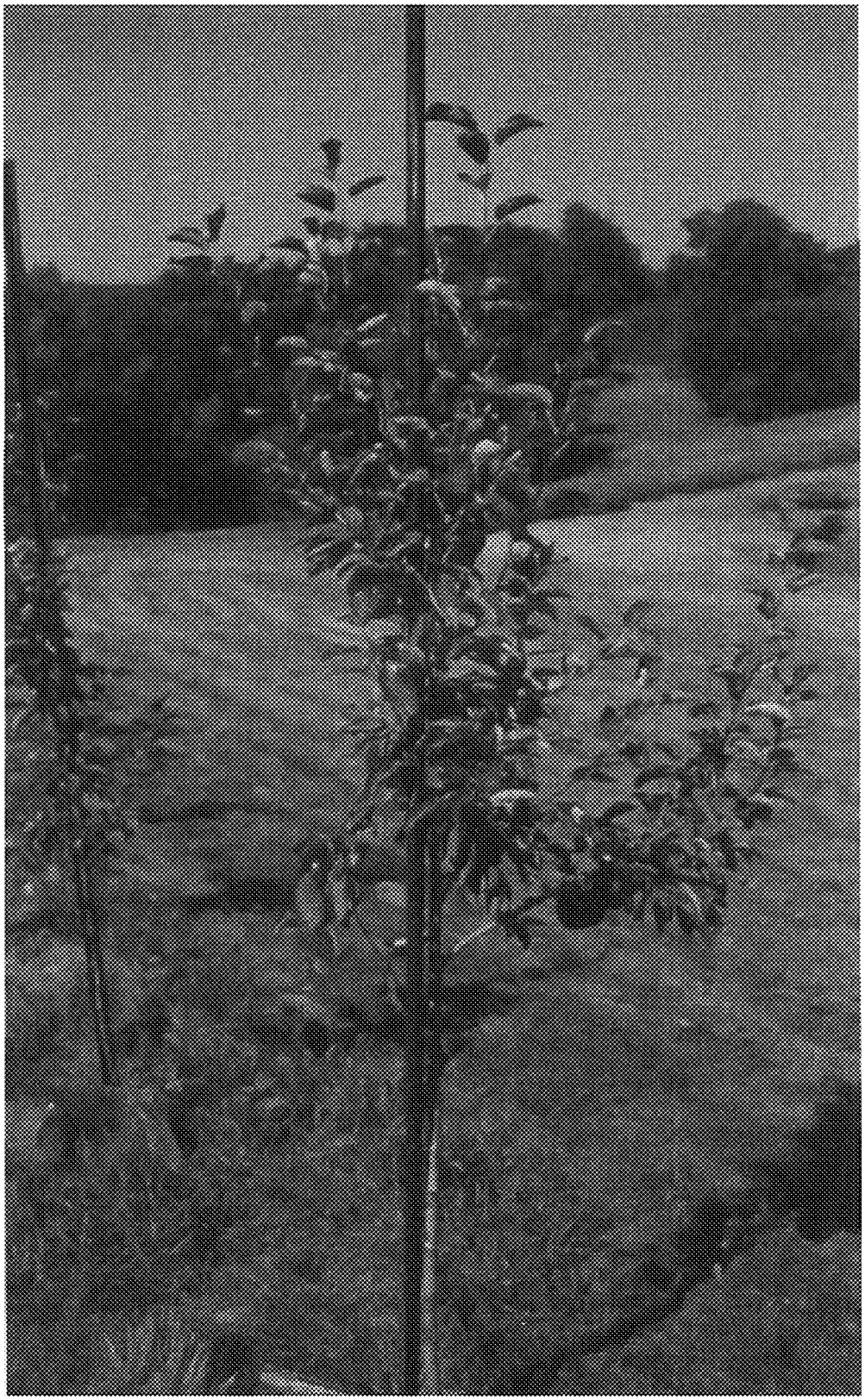

The second drawing illustrates the blossom of the new variety.

The third drawing illustrates a 2-year-old tree of the new variety.

DETAILED BOTANICAL DESCRIPTION

A detailed description of the 'PV 1027' cultivar follows using The Royal Horticultural Society of London Colour Chart for color identification except where general color terms are sufficient.

Parentage: A mutation of 'Arends' (U.S. Plant Pat. No. 2,800). Locality of the original discovery is Rogers, Ohio, USA.

Age of the observed tree is 5 years. The observed tree is budded on 'Malling 9 NIC 29' rootstock.

Location of observations is Van Buren County, Michigan, USA. This location is a USDA Zone 6 site at an elevation of 620 feet above sea level. The average date of last frost is April 15 with an average first freeze of October 15. Average yearly rainfall is 35 inches.

Tree:

*Age.*—5 years.
*Size.*—3.2 M in height, 2 M in width.
*Vigor.*—Vigorous, yearly growth averages 1 m.
*Density.*—Medium dense.
*Form.*—Upright, spreading.

*Production.*—Very productive, averaging 800 bushels per acre.
*Growth type.*—Non-spur.
*Bearing.*—Annual.

Trunk:
*Size.*—45 cm in diameter at 100 cm above ground level.
*Surface.*—Smooth.
*Bark color.*—Grey Group 20 B.
*Lenticel color.*—Grayed White 156D.
*Lenticels.*—Length 2 cm, width. 5 cm.
*Lenticel density.*—2 per $cm^2$.

Branches:
*Diameter 1 year.*—9 mm.
*Diameter 2 year.*—19 mm.
*Surface.*—Smooth.
*Branch color.*—Grayed-Purple 183A.
*Form.*—Profuse branching.
*Average angle.*—60°.
*Buds.*—Alternate, tightly applied to branch.
*Lenticels.*—Small, few, round to elongate.
*Lenticel color.*—White 158A.

Dormant leaf buds:
*Size.*—Length 4 cm, width 2 cm.
*Shape.*—Bluntly lanceolate.
*Color.*—Grayed Purple 187A.

Leaves:
*Size.*—Length 90 mm, width 50 mm.
*Form.*—Ovate.
*Texture.*—Crisp, tough.
*Leaf thickness.*—0.3 mm.
*Base.*—Rounded.
*Apex.*—Acute to slightly mucronate.
*Margin.*—Crenate.
*Pubescence.*—None on adaxial surface, fine pubescence on abaxial surface.
*Leaf color.*—Adaxial: Yellow-Green Group 147A. Abaxial: Yellow-Green Group 147C.
*Venation.*—Pinnate, 8 to 10 veins mainly alternate.
*Vein color.*—Adaxial: Yellow-green 147C. Abaxial: Yellow-Green 148C.
*Stipules.*—2, small, lanceolate, apex rounded, margin finely crenate, at base of petiole; length 8 mm, width. 5 mm.
*Stipule color.*—Yellow-Green 147C.
*Petiole.*—Slightly pubescent with single groove down entire length, very slightly indented.
*Petiole length.*—47 mm, diameter 2 mm at base, 2 mm at junction with leaf.
*Petiole color.*—Adaxial color Grayed Green 176C, abaxial color Yellow-Green 147C, pubescence color Grayed Green 176D.

Flower buds at popcorn stage:
*Pedicel.*—Length: 13 mm to 18 mm, diameter 2 mm.
*Pedicel color.*—Green 146 C.
*Bud.*—Length 9 mm, width 7 mm.
*Bud color.*—Red 56 D blush with background of White 155 D.

Flowers:
*Bloom timing.*—Early season.
*Blooming period.*—April 13 to 20 in Lawrence, Van Buren County, Mich.
*Pollination requirements.*—Viable pollen from another early season blooming apple variety such as 'Idared' (unpatented), 'Spartan' (unpatented) or 'Manchurian' (unpatented) crabapple. No known pollen incompatibilities have been discovered.
*Number of flowers per cluster.*—3 to 5.
*Fragrance.*—Very fragrant.
*Corolla diameter.*—24 mm to 32 mm.
*Stamens.*—20 to 25 in number, color White 155 D.
*Anther color.*—Yellow 14 B.
*Pollen.*—Profuse.
*Ovary.*—Pubescent, color Grayed Green 193 A.
*Pistil.*—Slightly lower than anthers in a majority of blossoms.
*Sepals.*—5 in number, length 4 mm, width 2 mm, pubescent, color Grayed Green 193 A.
*Petals.*—5 in number, length 11 mm, width 6 mm, slightly overlapping.
*Petal shape.*—Ovate, base rounded to cuneate at junction with receptacle, apex rounded, margin very slightly ruffled.
*Petal color.*—Adaxial: White 155 D. Abaxial: White 155 D.
*Petal texture.*—Soft.

Fruit:
*Maturity when described.*—Firm ripe. Penetrometer readings average 19 pounds at harvest and 17 pounds one month later. Average brix at harvest: 12% to 15%.
*Date of picking.*—August 21, in Rogers, Ohio, generally harvested in two to three pickings.
*Size.*—Axial diameter 90 mm, transverse diameter 55 mm.
*Average weight.*—1880 g to 2100 g.
*Form.*—Uniform, regular, reniform.
*Cavity.*—Obtuse, deep, depth 12 mm, breadth 20 mm.
*Basin.*—Symmetrical, abrupt at base, wide, depth, 12 mm, width 20 mm.
*Calyx.*—Open, segments persistent, erect, outer and inner surfaces pubescent.

Skin:
*Thickness.*—Thin.
*Texture.*—Very smooth, glossy with high cuticle wax, bloom present.
*Tendency to crack.*—Some, especially at stem end in high rain conditions.
*Lenticels.*—Inconspicuous, small, few in number, color White 155C.
*Color.*—Solid blush 90% Red 59A, with no striping.
*Ground color.*—Grayed Red 180A with Grayed Yellow 160A.

Flesh:
*Aroma.*—Sweet, aromatic.
*Color.*—Grayed-White 155 A.
*Texture.*—Firm, tender, fine, crisp.
*Eating quality.*—Best.

Core:
*Bundle area.*—Medium to ovate, cordate, symmetrical at base.
*Bundle.*—Inconspicuous, Yellow Green 145A, alternate above stamens.
*Capillary area.*—Distinct, medium large size.
*Calyx tube.*—Round to oblong, open.
*Depth of tube to shoulder.*—20 mm.
*Styles.*—Distinct, pubescent.
*Stamens.*—One distinct whorl, medium.
*Axillary cavity.*—Wanting.
*Seed cells.*—Walls thin, tough, length 10 mm, breadth 4 mm.
*Longitudinal section.*—Broadly ovate.

Seeds: Number perfect, 6 to 10.

*Number in one cell.*—1 to 2.

*Length.*—8 mm.

*Breadth.*—5 mm.

*Form.*—Obtuse, tufted.

*Color.*—Fan 4, Grayed-Orange, 175A.

Stem:

*Length.*—18 mm.

*Width.*—3 mm at base to 4 mm at end.

*Color.*—Grayed Purple 183B at base blending with Green 138C at abscission layer.

Use: Fresh market, dessert.

Shipping quality: Fair, not intended for long distance shipment. Local shipping quality is fair to good.

Keeping quality: Excellent, 30 to 60 days in common storage.

Tree winter hardiness: Above average for an apple variety. Tree is hardy to −20° to −35° F.

Bud winter hardiness: −15° to −20° F., depending on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases. No exceptional resistance to any major diseases of apple have been noted.

Graft incompatibilities: No specific graft incompatibilities have been noted.

I claim:

1. A new and distinct variety of apple tree, *Malus sylvestris,* substantially as herein shown and described, characterized particularly as to novelty by the unique combination of a vigorous, upright, spreading, medium density, regular bearing tree, producing fruits that mature 7 to 9 days before the parent and present a larger fruit with a more reniform shape and a shinier finish.

* * * * *